United States Patent [19]

King

[11] Patent Number: 4,849,400
[45] Date of Patent: Jul. 18, 1989

[54] FRAGRANCE COMPOSITION AND METHOD

[75] Inventor: Jerry King, Wichita, Kans.

[73] Assignee: Koch Industries, Inc., Wichita, Kans.

[21] Appl. No.: 230,838

[22] Filed: Aug. 10, 1988

[51] Int. Cl.$^4$ ................................................ A61K 7/46
[52] U.S. Cl. ........................................................ 512/2
[58] Field of Search ............................... 512/2; 585/25

[56] References Cited

U.S. PATENT DOCUMENTS

| | | | |
|---|---|---|---|
| 4,313,855 | 2/1982 | Klein et al. | 512/2 |
| 4,324,703 | 4/1982 | Seldner | 512/2 |

OTHER PUBLICATIONS

Terent-eve et al, Chem. Abst., vol. 57 #9698 (1962).
Sanin et al, Chem. Abst., vol. 60, #2346a (1964).
Beak et al, Tetrahedron, vol. 27(5), pp. 953–960 (1971).

Primary Examiner—James H. Reamer
Attorney, Agent, or Firm—Kokjer, Kircher, Bradley, Wharton, Bowman & Johnson

[57] ABSTRACT

A fragrance fixative and method of fixation of a fragrance along with a novel fragrance composition constitute the subject matter of the present invention. Phenylxylylethane and phenyltolylethane are known compounds which surprisingly exhibit superior qualities as a fragrance fixative. In addition to being desirable as a fragrance fixative, the compositions according to the invention exhibit desirable olfactory properties in and of themselves and can be useful in providing finishing touches to the bouquet or dominant note of the fragrance. The quantity of fixture utilized in carrying out the method and composition of the invention can vary over a wide range from 1-70% by weight. The fixative compositions can be combined with any known desirable fragrance composition.

11 Claims, No Drawings

FRAGRANCE COMPOSITION AND METHOD

This invention relates generally to fragrance compositions and, more particularly, to a novel composition, a method of preparing a fragrance composition, and a method of fixation of such a composition.

The science of fragrance creation has become a relatively complex field where dozens or even hundreds of different substances each having individual odor characteristics are combined to provide a composition with the desired olfactive effect. The various olfactory qualities of a fragrance composition are commonly referred to as "notes" with a dominant note providing the predominant olfactory effect and with more subtle notes providing support and finishing quality or "touches" to the dominant note. For example, when the formulater desires to provide a fragrance with a uniformly blended, fuller, rounder and more natural fragrance, i.e. to "finish" the fragrance, he/she will typically use a substance that can achieve subtle effects with minimal quantities. It is particularly with regard to the "finishing effects" that more distinctive and exclusive perfumes are distinguished from those that are more common.

As useful component in fragrance compositions is a "fixative" which can be defined as a compound which provides a prolonged lasting quality to a fragrance and aids in the equilization of differing rates of diffusion and evaporation of the original olfactory components.

It is, therefore, a primary object of the present invention to provide a fixative for fragrance compositions which is effective as a fixative and also supplements the various notes of the composition with a pleasing olfactory quality.

Another one of the objects of my invention is to provide a fixative for fragrance compositions which is compatible with a large number of different fragrances and is capable of rounding out the notes of the fragrance while imparting a lasting quality to the fragrance.

Another objective of the invention is to provide a method of preparing a fragrance utilizing a fixative according to the present invention.

Other objects of the invention will be made clear or become apparent from the following specification and claims.

Fragrance compositions are utilized in perfumes, cosmetics, creams, toilet soaps, bath salts, hair preparations, deodorants, lotions, sunscreens, face powders, and the like. They can also be utilized to improve the scent of detergents, cleaning agents, disinfectants and textile finishing agents. The foregoing are exemplary of the applications of the present invention.

Typical aromas which are desired in fragrance compositions include florals, rose, citrusy, muguet, fresh air, ozony, woody, piney, camphoraceous, leafy and green aromas, to name a few.

Most fragrance compositions fall into one of the following classifications: straight floral, floral bouquet, aldehydic, oriental, chypre, woody, green, citrus, fougere, musk (animal), leather, spice, herbal, and fruity. The following subclassifications for some of the more popular fragrance classes are listed below:

| | | | |
|---|---|---|---|
| Floral: | acacia | honeysuckle | marigold |
| | apple blossom | hyacinty | muguet |
| | carnation | iris | narcissus |
| | chamomile | jasmine | orange flower |
| | chrysanthemum | jonquil | rose |
| | clover | lavender | violet |
| | gardenia | lilac | mimosa |
| | heliotropine | lily | phlox |
| Citrus: | bergamot | mandarin | verbena |
| | orange | lime | lemon |
| | grapefruit | tangerine | |
| Woody: | cedar | juniper berry | hickory |
| | sandal | balsamic | |
| Green: | basil | moss | stringbean |
| | broken twig | parsley | varmouth |
| | cucumber | rhubarb | violet |
| | ivy | sea | watercress |
| | mimosa | | |
| Fruity: | apple | fig | pineapple |
| | apricot | grape | prune |
| | banana | melon | raspberry |
| | blackcurrant | peach | strawberry |
| | cherry | | |

It is to be understood that the term "fragrance composition" as used herein means a mixture of organic compounds which are admixed so that the combined odors produce a pleasant or desired fragrance. Such fragrance compositions usually contain: (a) the main note or "bouquet" or foundation stone of the composition; (b) modifiers which round off and accompany the main note; (c) fixatives which include odorous substances that lend a particular note to the perfume throughout all stages of evaporation and substances which retard evaporation; and (d) top notes which are typically low boiling fresh smelling materials. As previously indicated, it is the fixatives to which the present invention is particularly directed.

Phenylxylylethane and phenyltolylethane are known compositions. To the knowledge of the present applicant, however, neither compound has heretofore been utilized in fragrance compositions for any purpose. The compositions are readily available at relatively low cost and are generally stable. They are known to have a low order of toxicity.

Fixatives generally are cyclic oxygen containing compounds such as ethyl phthalate and isopropyl myrstate. It has been surprisingly found that compounds of the general formula

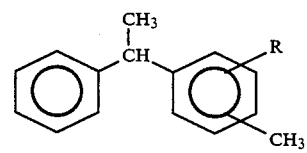

where
R=H or CH$_3$
can function as a fragrance fixative. Since there are no oxygen molecules present in the composition of the invention, its fixative properties are unexpected. Prior usages of compounds of the formula given above have been as dielectrics making the desirable odor characteristics of the compounds also surprising. While compounds having the diphenylmethane structure are known to possess a rose-like olfactory character and have been used in fragrance formulations heretofore, the odor is known to be weak and use of the compound is limited.

It has been found that incorporation of a compound represented by the formula set forth above greatly increases the strength and persistence of the desirable olfactory characteristics of a fragrance as compared with the diphenylmethane compound. In addition, as previously indicated, the composition of the structural formula given has highly desirable fixative properties. A quantity of anywhere from 1–75% (by weight) of the composition according to the present invention should be utilized with a range of 1–40% (by weight) being preferred and a quantity of 20–35% (by weight) being most preferred.

Phenylxylylethane may be prepared from styrene and orthoxylene utilizing sulfuric acid catalyst according to techniques well known to those skilled in the art. A suitable process for preparing phenylxylethane is set forth in Example 1.

EXAMPLE 1

O-xylene, 5096g, was charged to a 12 liter bottom outlet Pyrex reactor equipped with a mechanical agitator, heating mantle, addition funnel, cooling coil, thermometer, and a reflux condenser. Sulfuric acid, 981g of 96%, was charged in one portion with agitation. Styrene, 3749g, was added dropwise at 80°–85° C. over 90 min. The mixture was agitated for an additional 30 min. at 80°–85° C. after the styrene addition was complete. The mixture was allowed to settle for 45 min. and the lower sulfuric acid layer was drained off (1294.3g). A solution of sodium hydroxide (80g in 552g of water) was charged and the mixture was adjusted to 80° C. while agitating for 30 min. The mixture was allowed to settle for 30 min. and the lower sodium hydroxide layer was drained off (940.8g) at 80° C. Hot water (1440g) was charged and the mixture was agitated for 15 min. then allowed to settle for 30 min. The water wash was separated leaving 7982g of crude phenylxylylethane alkylate. The phenylxylylethane alkylate was vacuum fractionated to remove excess o-xylene then pure phenylxylylethane, BP 224° C. at 100 mmHg.

Phenyltolylethane may be prepared from styrene and toluene utilizing a sulfuric acid catalyst according to techniques well known to those skilled in the art. A typical procedure for preparing phenyltolylethane is set forth in Example 2.

EXAMPLE 2

Toluene 4423g was charged to a 12 liter bottom outlet Pyrex reactor equipped with a mechanical agitator, heating mantle, addition funnel, cooling coil, thermometer, and a reflux condenser. Sulfuric acid, 981g of 96% was charged in one portion with agitation. Styrene, 3749g, was added dropwise at 80°–85° over 90 min. The mixture was agitated for an additional 30 min. At 80°–85° C. after the styrene addition was complete, the mixture was allowed to settle for 45 min. and the lower sulfuric acid layer was drained off. A solution of sodium hyroxide (80g in 552g of water) was charged and the mixture was allowed to settle for 30 min, and the lower sodium hydroxide layer was drained off at 80° C. Hot water (1440g) was charged and the mixture was agitated for 15 min. then allowed to settle for 30 in. The water wash was separated leaving 7375g of crude phenyltolylethane alkylate. The phenyltolylethane alkylate was vacuum fractionated to remove excess toluene then pure phenyltolylethane, BP 205° C. 100 mmHg.

The compounds of the present invention have been Found to be relatively inert and stable in the presence of heat and light to temperatures as high as 200° C.

Examples 3, 4, 5 and 6 are typical fragrance formulations utilizing the fixative of the present invention.

EXAMPLE 3

| DETERGENT BOUQUET | |
|---|---|
| | % by weight |
| Benzophenone | 30 |
| Benzopyrone | 10 |
| Anisic Aldehyde | 60 |
| Musk Xylol | 60 |
| Amyl Salicylate | 30 |
| Alpha Amyl Cinnamic Aldehyde | 30 |
| Lilial | 45 |
| Eugenol | 10 |
| Styralyl Acetate | 10 |
| Geraniol | 50 |
| Indole 10% (ethanol solution) | 5 |
| Methyl Cinnamate | 15 |
| Oil Patchouly | 5 |
| Phenyl Ethyl Alcohol | 75 |
| Methyl Phenyl Acetate | 15 |
| Alpha Methyl Ionone | 50 |
| Terpineol | 100 |
| Methyl Para Cresol 10% | 5 |
| Oil Canaga | 10 |
| Diphenyl Oxide | 10 |
| Linalool | 200 |
| Phenyxylylethane | 175 |
| | 1000 |

EXAMPLE 4

| LAVANDER Fantasy | |
|---|---|
| Benzophenone | 10 |
| Coumarin | 20 |
| Musk Xylol | 35 |
| Phenyl Acetic Acid 10% | 5 |
| Alpha Amyl Cinnamic Aldehyde | 5 |
| Iso Butyl Phenyl Acetate | 5 |
| Phenyl Ethyl Acetate | 10 |
| Cyclamen Aldehyde | 10 |
| Geraniol | 20 |
| Benzyl Acetate | 10 |
| Allyl Caproate | 5 |
| Orange Oil | 15 |
| Lanandin | 50 |
| Benzyl Propionate | 30 |
| Aldehyde C—16 1% (by wt. in ethanol) | 20 |
| Iso Bornyl Acetate | 80 |
| Rosemary Oil | 100 |
| Citral | 10 |
| Oil Petitgrain | 10 |
| Terpineol | 80 |
| Geranyl Acetate | 20 |
| Phenyl Ethyl Iso Butyrate | 20 |
| Aldehyde C—11 1% | 30 |
| Methanyl Acetate | 200 |
| Phenylxylylethane | 200 |
| | 1000 |

EXAMPLE 5

| ROSE | |
|---|---|
| Aldehyde C—9 10% | 5 |
| Aldehyde C—11 10% | 5 |
| Linalool | 10 |
| Iso Butyl Phenyl Acetate | 300 |
| Phenyl Ethyl Alcohol | 140 |
| Geranyl Acetate | 20 |
| Citronellol | 100 |
| Oil Palma Rosa | 20 |
| Phenyl Ethyl Acetate | 50 |
| Phenylxylylethane | 350 |

-continued

| ROSE | |
|---|---|
| | 1000 |

EXAMPLE 6

| CARNATION | |
|---|---|
| Eugenol | 250 |
| Isoeugenol | 125 |
| Vanillin | 10 |
| Amyl salicylate | 50 |
| Benzyl salicylate | 50 |
| Phenylethyl alcohol | 60 |
| Phenylethyl acetate | 10 |
| Rhodinol | 100 |
| Phenylacetaldehyde | 10 |
| Ionone alpha | 20 |
| Carnation fragrance | 10 |
| Isoeugenol methyl ether | 30 |
| Ylang Ylang oil | 10 |
| Hydroxy citronellal | 20 |
| Terpineol | 50 |
| Tolu resinoid | 30 |
| Benzoid resinoid | 20 |
| Pimento oil | 10 |
| Phenyltolylethane | 135 |
| | 1000 |

It will be appreciated that the invention contemplates a method of preparing a fragrance which comprises the steps of combining a known fragrance producing composition with an olfactorily effective quantity of a compound according to the invention having the structural formula set forth above. The invention also contemplates a fragrance composition comprising 25°–99° by weight of a known fragrance producing composition and 1°–75° by weight of a compound of the invention according to the structural formula given above. The preferred formulation for the fragrance composition is 60–99% by weight of known fragrance components and 1–40% by weight of the formula according to the present invention.

Finally, the invention contemplates a method of fixation of a fragrance composition comprising the step of adding to the composition a compound of the structural formula previously given in a quantity sufficient to provide a measurable improvement in the lasting quality of the composition and to also equalize the evaporation and diffusion rates of the fragrance emitting notes.

I claim:

1. A method of preparing a fragrance comprising combining a known fragrance producing composition with an olfactorily effective quantity of a compound represented by the formula:

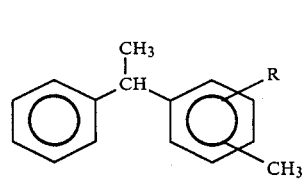

where
R=H or CH$_3$

2. A method as set forth in claim 1, wherein R=CH$_3$.

3. A method as set forth in claim 1, wherein said combining step comprises combining about 1–75% by weight of said compound with 25–99% by weight of said composition.

4. A method as set forth in claim 3, wherein said combining step comprises combining 1–40% by weight of phenyxylylethane with said known fragrance producing composition.

5. A fragrance composition comprising:
25–99% by weight of a known fragrance producing composition; and
1–75% by weight of a compound represented by the formula:

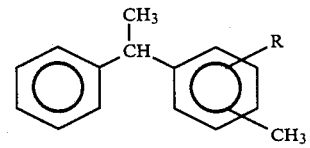

where
R=H or CH$_3$

6. A composition as set forth in claim 5 wherein R=CH$_3$.

7. A composition as set forth in claim 5, wherein said known fragrance producing composition comprises 60–99% by weight of said perfume composition and said compound comprises 1–40% by weight thereof.

8. A composition as set forth in claim 7, wehrein said compound comprises phenyxylylethane.

9. A method of fixation of a fragrance composition comprising adding to said composition a compound represented by the formula:

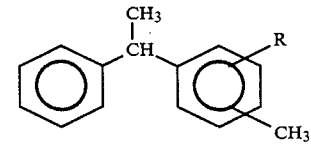

where
R=H or CH$_3$.

10. A method as set forth in claim 9, wherein R=CH$_3$.

11. A method as set forth in claim 9, wherein said adding step comprises adding about 1–75% by weight of said compound to 25–99% by weight of said composition.

* * * * *

UNITED STATES PATENT AND TRADEMARK OFFICE
CERTIFICATE OF CORRECTION

PATENT NO. : 4,849,400

DATED : July 18, 1989

INVENTOR(S) : Jerry King

It is certified that error appears in the above-identified patent and that said Letters Patent is hereby corrected as shown below:

Col. 6, line 10 should read: R = H or $CH_3$

Col. 6, line 41, "wehrein" should read "wherein"

Col. 6, line 55 should read: R = H or $CH_3$

Signed and Sealed this

Twenty-second Day of May, 1990

Attest:

HARRY F. MANBECK, JR.

Attesting Officer     Commissioner of Patents and Trademarks